United States Patent
Effenberger et al.

(10) Patent No.: US 6,465,222 B1
(45) Date of Patent: Oct. 15, 2002

(54) METHOD FOR STEREOSELECTIVE PRODUCTION OF SUBSTITUTED CYCLOHEXYLANHYDRINS

(75) Inventors: Franz Effenberger, Stuttgart; Jürgen Roos, Freigericht; Reiner Fischer, Monheim, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/701,314

(22) PCT Filed: May 20, 1999

(86) PCT No.: PCT/EP99/03464

§ 371 (c)(1),
(2), (4) Date: Nov. 28, 2000

(87) PCT Pub. No.: WO99/63104

PCT Pub. Date: Dec. 9, 1999

(30) Foreign Application Priority Data

Jun. 2, 1998 (DE) .......................................... 198 24 491

(51) Int. Cl.[7] .......................... C12P 13/00; C07C 211/00
(52) U.S. Cl. ..................................... 435/128; 435/280
(58) Field of Search .................................. 435/280, 128

(56) References Cited

PUBLICATIONS

Albrecht et al., "Improved Purification of an (R)–oxynitrilase from Linum usitatissium (flax) and investigation of the substrate range", Biotechnol. Appl. Biochem. 17 (2) : 191–203 (1993).*

Beyer, Walter, Lehrbuch der Organischen Chemie (Textbook of Organic Chemistry), 21st edition, S. Hirzel Verlag Stuttgart, 1988, pp. 213–216 and pp. 535–537, "21., Völlig Neu Bearbeitete und Erweiterte Auflage, Mit 138 Abbildungen und 20 Tabellen".

Synthesis, Jun./Jul., 1985, pp. 645–674, V. I. Ognyanov et al, "Palladium–Catalyzed Synthesis of 2-Allyl-2-Nitrocycloalkanones".

Bull. Chem. Soc. Chim Fr 4, 1970, pp. 1435–1439, Max Mousseron et al, "No. 247–Obtention de Dérivés de la Phényl–1 Cyclohexylamine Comportant un Groupe Phényle en Axial".

Bull. Soc. Chim. Fr. 11, 1980, pp. 187–191, P. Geneste et al, "Approche de la Synthése d'β–Aminonitriles en Milieu Organique Anhydre".

J. Org. Chem, 47, 1982, pp. 3881–3886, P. W. Jeffs et al, "Synthesis of (±)–Mesembranol and (±)–O–Methyljoubertiamine. Aza–Ring Expansion of cis–Bicyclo[4.2.0]octanones[1]".

Chem. Commun., 1997, pp. 1933–1940, H. Griengl et al, "Enzymatic Cleavage and Formation of Cyanohydrins: A Reaction of Biological and Synthetic Relevance".

Angew. Chem., 106, 1994, pp. 1609–1619, F. Effenberger, "Synthese und Reaktionen Optisch Aktiver Cyanhydrine".

Angew. Chem. Int. Ed. Engl. 35, No. 4, 1996, pp. 437–439, S. Förster, et al, "The First Recombinant Hydroxynitrile Lyase and Its Application in the Synthesis of (S)–Cyanohydrins".

Enantiomer, vol. 1, pp. 359–363, F. Effenberger, "Optically Active Cyanohydrins–Important Sources for Chiral Drugs" (1996).

Biochem Z. 337, 1963, pp. 156–166, W. Becker et al, "Zur Kenntnis der Cyanhydrinsynthese II. Reindarstellung und Eigenschaften der Oxynitrilase aus Bitteren Mandeln (Prunus Communis Stokes)".

Biochem. Z. 346, 1966, pp. 301–321, W. Becker et al, "Über das Flavinenzym D–Oxynitrilase".

Proteins, 19, 1994, pp. 343–347, H. Lauble, et al, "Crystallization and Preliminary X–Ray Diffraction Studies of Mandelonitrile Lyase From Almonds".

Helvetica Chim. Acta, vol. 66, Fasc. 2, Nr. 42, 1983, pp. 489–493, von Erich Hochuli, "42. Reinigung der D–Oxynitrilase aus Mandeln mit Hilfe der Affinitäts–Chromatographie".

University of California, Davis, Mar. 25, 1981, pp. 1–252, F. J. P. DeCampas Carvalho, "Dissertation".

Arch. Biochem. & Biophys., vol. 311, No. 2, Jun. 1994, pp. 496–502, J. Hughes et al, "Purification, Characterization, and Cloning of α–Hydroxynitrile Lyase from Cassava (*Manihot esculenta* Crantz)".

Physiologia Plantarum 75, 1989, pp. 97–100, D. Selmar et al, "α–Hydroxynitrile Lyase in *Hevea brasiliensis* and Its Significance for Rapid Cyanogenesis".

Plant Science, 115, 1996, pp. 25–31, H. Wajant et al, "Purification and Characterization of Hydroxynitrile Lyase from *Hevea Brasiliensis*".

Tetrah. Letters, vol. 29, No. 35, 1988, pp. 4485–4488, J. Brussee et al, "Bio–Organic Synthesis of Optically Active Cyanohydrins and Acyloins".

Tetrah. Asymmetry, vol. 7, No. 4, 1996, pp. 1105–1116, E. Kiljunen et al, "(R)–and (S)–Cyanohydrins Using Oxynitrilases in Whole Cells".

Synthetic Communications, 21, 1991, pp. 1387–1391, P. Zandbergen et al, "Synthesis of Optically Active Cyanohydrins Using Almond Meal".

* cited by examiner

*Primary Examiner*—Sandra E. Saucier
*Assistant Examiner*—Vera Afremova
(74) *Attorney, Agent, or Firm*—Joseph C. Gil; Richard E. L. Henderson

(57) ABSTRACT

The invention relates to a process for the stereoselective preparation of cyclohexylcyanohydrins by reaction of 4-substituted cyclohexanones with a cyanide source in the presence of an oxynitrilase.

2 Claims, No Drawings

METHOD FOR STEREOSELECTIVE PRODUCTION OF SUBSTITUTED CYCLOHEXYLANHYDRINS

BACKGROUND OF THE INVENTION

The present invention relates to a new process for the stereoselective preparation of substituted cyclohexylcyanohydrins.

It is known that cyanohydrins can be prepared by reaction of ketones with hydrocyanic acid (see, for example, Beyer, Walter, Lehrbuch der Organischen Chemie [Textbook of Organic Chemistry], 21$^{st}$ Edition, S. Hirzel Verlag Stuttgart 1988, page 213). In substituted cyclic ketones, however, this reaction does not proceed stereoselectively with sterically less demanding radicals.

Protected cyanohydrins are obtained in the reaction of ketones with trimethylsilyl cyanide (see the reference cited above, Beyer, Walter p. 535 ff., Hiyama, Saito, Synthesis 1985, 645–647). The use of oxynitrilases for the preparation of optically active cyanohydrins is also known (see, for example, EP-A-0 799 894).

It was the object of the present invention to make available a process for the more stereoselective preparation of substituted cyclohexylcyanohydrins.

SUMMARY OF THE INVENTION

The present invention relates to a process for the stereoselective preparation of cyclohexylcyanohydrins of the formula (I)

(I)

in which
R represents alkyl, cycloalkyl (in which a methylene group is optionally replaced by oxygen), alkoxy, alkenyloxy, cycloalkyloxy, arylalkyloxy, aryloxy or aryl, in each case optionally substituted,
which is characterized in that cyclohexanones of the formula (II)

(II)

in which
R has the abovementioned meanings,
are reacted with a cyanide source in the presence of an oxynitrilase and if appropriate in the presence of a diluent.

DETAILED DESCRIPTION OF THE INVENTION

The wavy line in the formula (I) means that the compounds of the formula (I) are mixtures of cis and trans isomers of the following structure:

cis    trans

Surprisingly, the compounds of the formula (I) are obtained in good yield. Reactions of cycloalkanones with oxynitrilases to give cyanohydrins were not known.

Furthermore, the process according to the invention proceeds more rapidly than the purely chemical process.

The process according to the invention furthermore surprisingly yields, depending on the oxynitrilase employed, an excess of desired isomers (cis or trans).

The process according to the invention can be represented by the following equation if hydrocyanic acid is used as a cyanide source:

Formula (II) provides a general definition of the compounds needed as starting substances for the process according to the invention.

Preferred substituents or ranges of the radical R shown in the formulae mentioned above and below are explained below.

Compounds preferably employed in the process according to the invention are those of the formula (II) in which
R represents $C_1$–$C_8$-alkyl which is optionally substituted by halogen, $C_3$–$C_8$-cycloalkyl (in which one methylene group is optionally replaced by oxygen) which is optionally substituted by $C_1$–$C_6$-alkyl or $C_1$–$C_6$-alkoxy, $C_1$–$C_8$-alkoxy which is optionally substituted by halogen, $C_3$–$C_6$-alkenyloxy which is optionally substituted by halogen, $C_2$–$C_8$-cycloalkyloxy which is optionally substituted by $C_1$–$C_6$-alkyl or $C_1$–$C_6$-alkoxy, or phenyl, phenoxy or benzyloxy, each of which is in each case optionally substituted by halogen, $C_1$–$C_6$-alkyl, $C_1$–$C_6$-halogenoalkyl, $C_1$–$C_6$-alkoxy or $C_1$–$C_6$-halogenoalkoxy.

Compounds particularly preferably employed are those of the formula (II) in which
R represents $C_1$–$C_6$-alkyl which is optionally substituted by halogen, $C_3$–$C_6$-cycloalkyl (in which a methylene group is optionally replaced by oxygen) which is optionally substituted by $C_1$–$C_4$-alkyl or $C_1$–$C_4$-alkoxy, $C_1$–$C_6$-alkoxy which is optionally substituted by halogen, $C_3$–$C_6$-alkenyloxy which is optionally substituted by halogen, $C_3$–$C_6$-cycloalkyloxy which is optionally substituted by $C_1$–$C_4$-alkyl or $C_1$–$C_4$-alkoxy, or phenyl, phenoxy or benzyloxy, each of which is in each case optionally substituted by halogen, $C_1$–$C_4$-alkyl, $C_1$–$C_2$-halogenoalkyl, $C_1$–$C_4$-alkoxy or $C_1$–$C_2$-halogenoalkoxy.

Halogen in the above definitions represents fluorine, chlorine, bromine and iodine, particularly fluorine, chlorine and bromine, in particular fluorine and chlorine.

Compounds very particularly preferably employed are those of the formula (II) in which R is methyl, ethyl, n-propyl, i-propyl, n-butyl, i-butyl, tert-butyl, cyclopentyl, cyclohexyl, allyloxy, 2-butenyloxy, methoxy, ethoxy, n-propoxy, isopropoxy, n-butoxy, isobutoxy, tert-butoxy, phenyl or benzyloxy.

In particular, the following compounds of the formula (II) may be mentioned:

| | |
|---|---|
| 4-methylcyclohexanone | 4-methoxycyclohexanone |
| 4-ethylcyclohexanone | 4-ethoxycyclohexanone |
| 4-n-propylcyclohexanone | 4-n-propoxycyclohexanone |
| 4-isopropylcyclohexanone | 4-isopropoxycyclohexanone |
| 4-n-butylcyclohexanone | 4-n-butoxycyclohexanone |
| 4-isobutylcyclohexanone | 4-isobutoxycyclohexanone |
| 4-tert-butylcyclohexanone | 4-tert-butoxycyclohexanone |
| 4-cyclohexylcyclohexanone | 4-allyloxycyclohexanone |
| 4-phenylcyclohexanone | 4-benzyloxycyclohexanone |

The compounds of the formula (I) prepared according to the invention are known in some cases or can be prepared by the processes described in the literature cited at the beginning (M. Mousseron et. Al.; Bull. Soc. Chim. Fr. 4. 1435–39 (1970); P. Geneste et. al.; Bull. Soc. Chim. Fr., II, 187–191 (1980)).

The compounds of the formula (II) needed as starting substances for carrying out the process according to the invention are known in some cases or can be prepared by processes which are known in principle (compare Example II-1 and, for example, J. Org. Chem. 47 3881, 1982).

The process according to the invention is preferably carried out in the presence of a diluent which is inert to the reactants.

Aliphatic or aromatic hydrocarbons, such as benzine, toluene, xylene and tetralin, can preferably be used, in addition aliphatic or aromatic halogenohydrocarbons, such as methylene chloride, chloroform, carbon tetrachloride, chlorobenzene and o-dichlorobenzene, furthermore open-chain or cyclic ethers, such as diethyl ether, methyl tert-butyl ether, diisopropyl ether, tetrahydrofuran and dioxane, in addition carboxylic acid esters, such as ethyl acetate, and also strongly polar solvents, such as dimethyl sulphoxide and sulpholane, or alternatively alcohols such as methanol, ethanol, isopropanol and tert-butanol.

Preferred diluents are ethers (in particular dilsopropyl ether) and carboxylic acid esters (in particular ethyl acetate).

The reaction according to the invention can also be carried out in a two-phase system which consists of water and an organic solvent which is not completely miscible with water. For this, suitable organic solvents are, for example, methyl tert-butyl ether, diisopropyl ether and ethyl acetate. Diisopropyl ether is preferably used.

The process according to the invention can also be carried out in an aqueous system in the absence of an organic solvent at a preferred pH of <5, in particular at a pH of between 3 and 4. The pH is adjusted by means of a buffer. Suitable buffers are, for example, sodium acetate or sodium citrate. Preferably, a 20 to 500 mM sodium citrate buffer is used.

The process according to the invention is carried out in the presence of an oxynitrilase (hydroxynitrile lyase). Oxynitrilases are enzymes which catalyse the cleavage and formation of cyanohydrins. Oxynitrilases have long been known (see, for example, EP-A-0 799 894; Chem. Commun. 1997, 1933; Angew. Chem. 1994, 106, 1609–1619; Angew. Chem. Int. Ed. Engl. 1996, 35, 438; Enantiomer, Vol. 1, pp. 359–363).

For the process according to the invention, the following oxynitrilases are preferably employed: (R)-oxynitrilase from the bitter almond (Prunus amygdalus), (S)-oxy-nitrilase from cassava (Manihot esculenta) and (S)-oxynitrilase from the rubber tree (Hevea brasiliensis). The (R)-oxynitrilase from the bitter almond (Prunus amygdalus) and the (S)-oxynitrilase from cassava (Manihot exculenta) are particularly preferably employed. The (R)-oxynitrilase from the bitter almond (Prunus amygdalus) is very particularly preferably used.

Depending on the type of oxynitrilase employed, the process according to the invention leads to an excess of trans or cis isomers. In some cases, a dependence of the reaction course on the type of substituent R is moreover to be observed.

The use of the (R)-oxynitriliase from bitter almond basically leads to an excess of trans isomers.

When using the (S)-oxynitrilase from cassava, the trans isomer surprisingly predominates for the small radicals R methyl and methoxy, while for larger radicals R an excessively cis isomer is regularly obtained.

With smaller radicals R (for example methoxy), the use of the (S)-oxynitrilase from the rubber tree likewise yields an excess of trans isomers.

The obtainment of the oxynitrilases mentioned is described in the literature.

For the isolation of the (R)-oxynitrilase [EC 4.1.2.10] from bitter almonds see, for example, Biochem. Z. 1963, 337, 156–166 and 1966, 346, 301–321; Proteins 1994, 19, 343–347; Helv. Chim. Acta, 1983, 66, 489. For the isolation of the (S)-oxynitrilase [EC 4.1.2.37] from cassava see, for example, F. J. P. De C. Carvalho, Dissertation, University of California, Davis, 1981; Arch. Biochem. Biophys. 1994, 311, 496–502. For the isolation of the (S)-oxynitrilase from the rubber tree see, for example, Physiologia Plantarum 1989, 75, 97; Plant Science 1996, 115, 25–31.

Basically, the oxynitrilases can be employed in the process according to the invention in various preparation forms.

On the other hand, crude enzyme can also be used, i.e. the enzyme is not isolated, but a cell-free extract is employed which is obtained by disrupting the cells with ultrasound, centrifuging off the crude extract thus obtained from the cell walls/membranes and concentrating it. References, e.g. (R)-oxynitrilase: Tetrah. Lett. 1988, 29, 4485–88, Tetrah. Ass. 1996, 7, 1105–1116, Synthetic Communications 1991, 21, 1387–91.

For the use of (R)-oxynitriles from bitter almonds, the use of preferably defatted almond flour which is obtained by grinding bitter almonds and extracting them with, for example, hexane or petroleum ehter (commercially available from Sigma) or ref.: Lett., 1988, 29, 4485–4488 is suitable.

Purified enzyme is preferably used.

The enzymes can be bound to suitable carrier material for carrying out the reaction according to the invention. Suitable carrier materials are, for example, celluloses, in particular nitrocellulose and cellulose P 100 PSC: Elcema®; Degussa, particle size 50–150 µm, coated on the surface with 2% of amorphous silicic acid (Aerosil). After the reaction is complete, this procedure makes possible the removal of carrier-bound enzyme by filtration and thus the simplified work-up. The carrier-bound enzyme thus recovered can moreover be used again.

As a rule, the enzyme is applied to the carrier by adding the enzyme solution dropwise to the carrier, see also, for example, Angew. Chem. Int. Ed. Engl. 1996, 35, 439.

The process according to the invention is carried out in the presence of a cyanide source.

Suitable cyanide sources are all compounds which release cyanide ions ($CN^-$). Examples which may be mentioned are hydrocyanic acid, cyanohydrins such as acetone cyanohydrin and metal cyanides such as KCN. Hydrocyanic acid or KCN, particularly preferably hydrocyanic acid, is preferably used.

The temperature in the process according to the invention can be varied within a relatively large range. In general, the reaction is carried out at temperatures between −20° C. and 80° C., preferably between 0° C. and 40° C.

The process according to the invention is in general carried out under normal pressure.

The molar ratio of compound of the formula (II) to cyanide ions is in general between 1:1 and 1:50, preferably between 1:1 and 1:4.

In general, when carrying out the process according to the invention, the compound of the formula (II) and the cyanide source are introduced into a suitable diluent, the immobilized enzyme is added and the reaction mixture is stirred at room temperature until the reaction is complete. The catalyst is then filtered off and the filtrate is worked up using customary methods.

In principle, it is also possible to carry out the reaction continuously, for example, by passing the starting materials dissolved in the diluent through a column which is loaded with the carrier-immobilized enzyme or allowing them to react in a membrane reactor, the products being separated from the starting materials and the catalyst by evaporation.

The compounds of the formula (I) prepared using the process according to the invention are valuable intermediates for the preparation of herbicides and pesticides according to the following reaction scheme: (see, for example, EP 0 647 637).

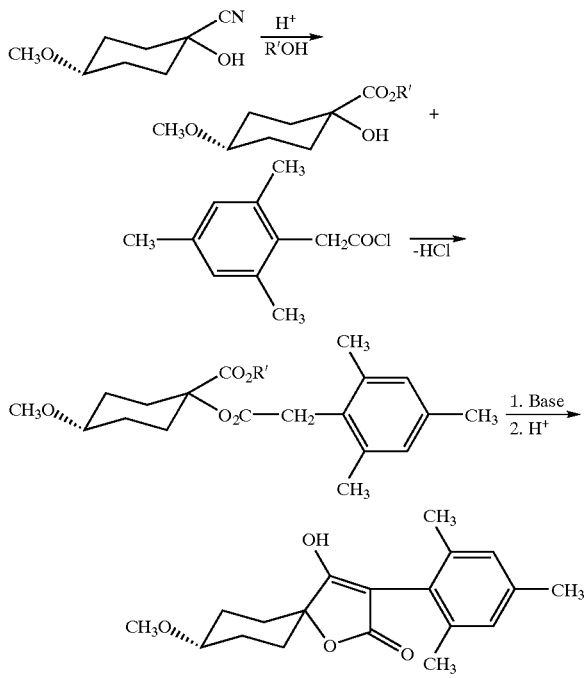

EXAMPLES

Example 1
(Substrate Concentration 0.2 mol/l)

The enzyme immobilized on cellulose (*Prunus amygdalus*) or nitro-cellulose was added to a solution of 1 mmol of ketone and 3.9 mmol of hydrocyanic acid in 5 ml of diisopropyl ether and the mixture was stirred at room temperature for the time indicated.

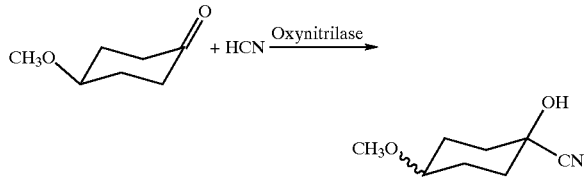

| Enzyme from | Units/mmol | Reaction period (h) | Conversion* (%) | Isomer ratio* (trans:cis) |
|---|---|---|---|---|
| a) *Prunus amygdalus* | 100 | 4.5 | 92 | 92:8 |
| b) *Manihot esculenta* | 100 | 1 | quant. | 70:30 |
| c) *Hevea brasiliensis* | 1000** | 2 | quant. | 65:35 |

*The non-enzyme-catalysed competition reaction is of no consequence here: it reaches only 6% conversion in 10 hours with an isomer ratio of 54:46 (cis:trans)
**Activity test using (S)-mandelonitrile as a substrate The enzymes were obtained and applied to the carriers by the following procedures:

The enzyme solution of the (R)-oxynitrilase from *Prunus amygdalus* is added to the cellulose carrier which has previously been swollen in a sodium citrate buffer (20 mM, pH 3.3) and then pressed off. The enzyme-loaded carrier is used directly as such The enzyme solutions of the two (S)-oxynitrilases are added to nitrocellulose which has likewise previously been swollen in a sodium citrate buffer (20 mM, pH 3.3) and then dried in a high vacuum. The enzyme-loaded carrier is centrifuged in order to remove the excess water (Angew. Chem. Int. Ed. Eng. 1996 35, No. 4, 437–439).

(R)-Oxynitrilase from the bitter almond were used in Examples 2 to 5 below (100 U of the enzyme per 1 mmol of ketone) and the following reaction was carried out:

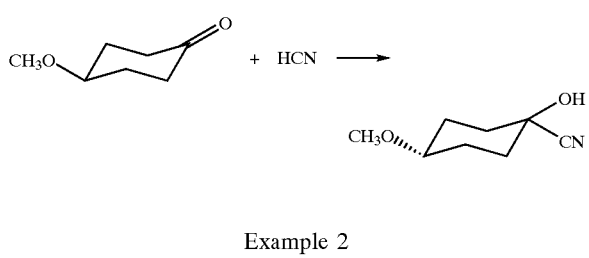

Example 2
(Substrate Concentration 0.2 mol/l)

| Solvent | Reaction period (h) | Conversion (%) | Isomer ratio (trans:cis) |
|---|---|---|---|
| a) Diisopropyl ether | 4.5 | 92 | 92:8 |
| b) tert-Butylmethyl ether | 23 | 82 | 87:13 |
| c) Ethyl acetate | 24 | 17 | 74:26 |

Example 3
(Substrate Concentration 0.2 mol/l)

On variation of the carrier material, the lowering of the water content on the carrier was especially predominant. By means of centrifugation of the nitrocellulose loaded with enzyme solution, it was possible to lower the water content very greatly.

| Carrier | Reaction period (h) | Conversion (%) | Isomer ratio (trans:cis) |
|---|---|---|---|
| a) Cellulose P100PSC | 4.5 | 92 | 92:8 |
| b) Nitrocellulose | 7 | 62 | 91:9 |

Example 4

(Substrate Concentration 0.2 mol/l)

| Reaction temperature (°C.) | Reaction period (h) | Conversion (%) | Isomer ratio (trans:cis) |
|---|---|---|---|
| a) 0 | 1 | 41 | 91:9 |
| b) 25 | 2 | 74 | 91:9 |
| c) 42 | 2 | quant. | 89:11 |

Example 5

| Substrate concentration [M] | Reaction period (h) | Conversion (%) | Isomer ratio (trans:cis) |
|---|---|---|---|
| a) 0.2 | 4.5 | 92 | 92:8 |
| b) 0.6 | 2 | quant. | 90:10 |
| c) 1.0 | 2 | 87 | 82:18 |

Example 6

(R)-Oxynitrilase-catalysed Addition of Hydrocyanic Acid to Cyclohexanone Derivatives All reactions were carried out in diisopropyl ether and at room temperature. The (R)-oxynitrilase was adsorbed on cellulose which had previously been swollen in 20 mM citrate buffer solution pH 3.3. Hydrocyanic acid was added to the substrate in a four-fold excess. For each enzyme batch, a blank sample was carried out in order to be able to estimate the chemical reaction.

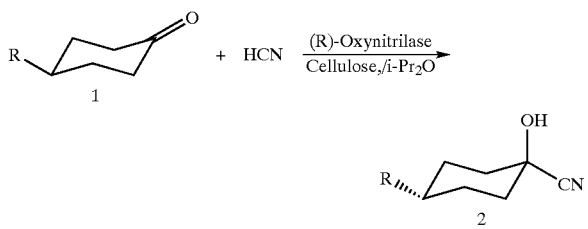

TABLE 1

| | | | Cyanohydrin 2 | | Blank sample [b] | |
|---|---|---|---|---|---|---|
| R | U/mmol | t [h] | Conversion [%] | cis/trans [a] [%] | Conversion [%] | cis/trans [a] [%] |
| Methyl- | 200 | 1.5 | 99 | 3:97 | 4 | 17:83 |
| Ethyl- | 200 | 7.25 | 92 | 2:98 | <0.5 | n.d. [c] |
| Propyl- | 200 | 22 | 73 | 2:98 | <1 | n.d. |
| isoPropyl- | 200 | 22 | 94 | 1:99 | <1 | n.d. |
| tert-Butyl- | 200 | 216 | 50 | 10:90 | 2 | 13:87 |
| Ethoxy- | 200 | 24 | 99 | 11:89 | 78 | 43:57 |
| Propoxy | 200 | 48 | 60 | 14:86 | 21 | 46:54 |
| Phenyl- | 200 | 360 | 83 | 5:95 | 49 | 10:90 |

[a] Isomer ratio after acetylation with dimethylaminopyridine and acetic anhydride determined by gas chromatography.
[b] Instead of the enzyme solution, a corresponding amount of a 20 mM sodium acetate buffer pH 5.4 was used.
[c] Not determined.

Example 7

(S)-Oxynitrilase-catalysed Addition of Hydrocyanic Acid to Cyclohexanone Derivatives For the reactions of (S)-oxynitrilase from cassava (Manihot esculenta), except for nitrocellulose as a new enzyme carrier material, the same optimized reaction conditions were chosen as for the (R)-oxynitrilase from bitter almonds.

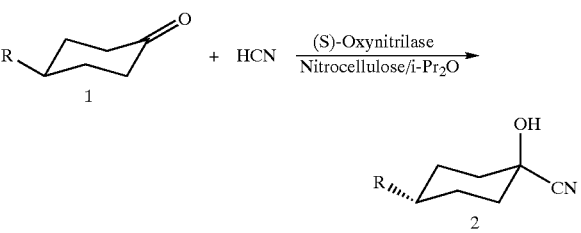

TABLE 2

| | | | Cyanohydrin 2 | | Blank sample | |
|---|---|---|---|---|---|---|
| R | U/mmol | t [h] | Conversion [%] | IV cis/trans [a] [%] | Conversion [%] | cis/trans [%] |
| Methyl- | 100 | 2 | 99 | 35:65 | | |
| Ethyl- | 100 | 3 | 93 | 74:26 | <0.5 | n.d. [b] |
| Propyl- | 100 | 5 | 96 | 96:4 | <1 | n.d. |
| isoPropyl- | 100 | 5 | 93 | 97:3 | <1 | n.d. |
| tert-Butyl | 100 | 3 | 82 | 99:1 | | |
| Ethoxy- | 100 | 1 | 99 | 61:39 | | |
| Propoxy- | 100 | 2 | 91 | 87:13 | | |
| Phenyl- | 100 | 3 | 95 | 99:1 | | |

[a] Isomer ratio after acetylation with dimethylaminopyridine and acetic anhydride determined by gas chromatography.
[b] Not determined

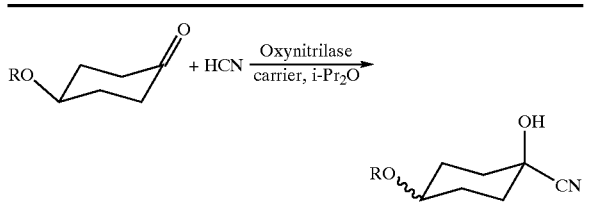

| R | Reaction period [h] | Conversion [%] | Isomer ratio cis:trans |
|---|---|---|---|
| (R)-Oxynitrilase from bitter almonds | | | |
| Allyl- | 22 | 97 | 8:92 |
| i-Butyl- | 46 | 18 | 16:84 |
| (S)-Oxynitrilase from cassava | | | |
| Allyl- | 3 | 99 | 87:13 |
| i-Butyl- | 46 | 52 | 90:10 |

| R | Reaction period [h] | Conversion [%] | Isomer ratio cis:trans |
|---|---|---|---|
| Allyl- | 22 | 17 | 45:55 |
| i-Butyl- | 46 | 2 | 53:47 |

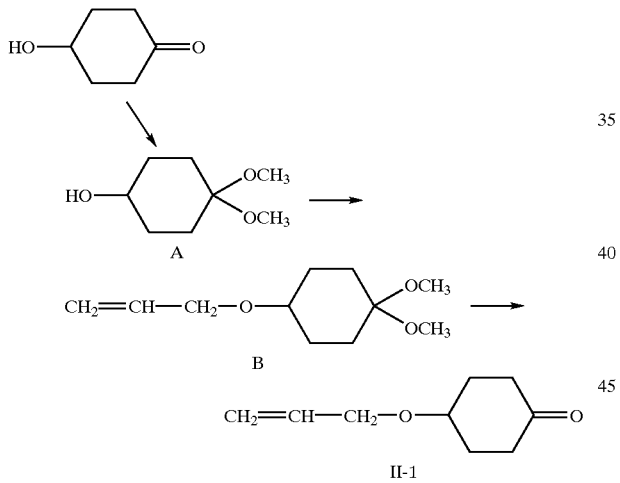

Preparation of Compound A 94 g of commercially available 4-hydroxycyclohexanone in 275 ml of trimethyl ortho-formate are treated at room temperature with 260 g of methanol and 5 mg of para-toluenesulfonic acid in 20 ml of methanol and the mixture is refluxed for 10 minutes. It is then neutralized at about 0C with aqueous sodium hydrogencarbonate solution and concentrated. The residue is chromatographed on silica gel using the eluent hexane/acetone 7/3.

Yield: 125 g (95% of theory).

Preparation of Compound B 150 g of potassium tert-butoxide and 151 g of allyl bromide are added at room temperature to 200 g of compound A in 1500 ml of tert-butanol and the mixture is stirred at about 60° C. for one day. It is then diluted with water, extracted with methylene chloride and the organic phase is concentrated. The residue is chromatographed on silica gel using the eluent hexane/acetone 10/1.

Yield: 215 g (86% of theory).

Preparation of compound (II-1)

233 g of compound 3 are stirred at room temperature for 2 hours in 1000 ml of tetrahydrofuran (THF) and 750 ml of 1 N HCl. The mixture is then treated with water and extracted with methylene chloride. The organic phase is concentrated.

Yield: 157 g (88% of theory).

What is claimed is:

1. A process for the stereoselective preparation of cyclohexylcyanohydrins of the formula (I)

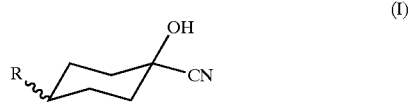

wherein R represents an alkyl, cycloalkyl in which a methylene group is optionally replaced by oxygen, alkoxy, alkenyloxy, cycloalkyloxy, arylalkyloxy, or aryl group, each such group being optionally substituted, comprising reacting a cyclohexanone of the formula (II)

wherein R has the same meanings as for formula (I), with a cyanide source in the presence of an oxynitrilase and optionally in the presence of a diluent.

2. A process for the preparation of a trans-cyclohexylcyanohydrin of the formula (Ib)

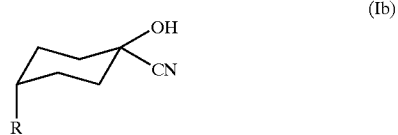

wherein R represents an alkyl, cycloalkyl in which a methylene group is optionally replaced by oxygen, alkoxy, alkenyloxy, cycloalkyloxy, arylalkyloxy, or aryl group, each such group being optionally substituted, comprising reacting a cyclohexanone of the formula (II)

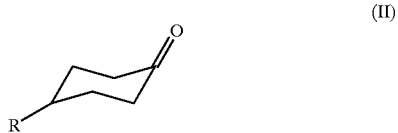

wherein R has the same meanings as for formula (Ib), with a cyanide source in the presence of (R)-oxynitrilase from bitter almond and optionally in the presence of a diluent.

* * * * *